United States Patent [19]

Omura et al.

[11] 4,199,514

[45] Apr. 22, 1980

[54] COMPOUND, FRENOLICIN B WHICH IS USEFUL AS AN ANTIBIOTIC

[75] Inventors: Satoshi Ômura, Tokyo; Yuzuru Iwai, Narita; Juichi Awaya, Souka; Yoko Takahashi, Tokyo; Ruiko Ôiwa, Yokohama, all of Japan

[73] Assignee: The Kitasato Institute, Tokyo, Japan

[21] Appl. No.: 6,461

[22] Filed: Jan. 25, 1979

[30] Foreign Application Priority Data

Feb. 17, 1978 [JP] Japan .................................. 53-16452

[51] Int. Cl.$^2$ ........................................... C07D 493/04
[52] U.S. Cl. .............................. 260/343.3 R; 435/119; 435/886
[58] Field of Search ................................ 260/343.3 R

[56] References Cited

U.S. PATENT DOCUMENTS 3,564,019   2/1971   Holmlund et al. ............. 260/343.3 R

OTHER PUBLICATIONS

Chem. Abst., vol. 85, 2246cs.
Bergy, J. Antibiotics 21, 454–457, 1968.

Omura et al., Jour. Chem. Soc. Chem. Commun. 320–321, 1976.

*Primary Examiner*—Natalie Trousof
*Assistant Examiner*—Jane T. Fan
*Attorney, Agent, or Firm*—Frishauf, Holtz, Goodman & Woodward

[57] ABSTRACT

A novel compound frenolicin B of the formula:

is prepared by cultivating a microorganism belonging to genus Streptomyces, e.g. *Streptomyces roseofulvus* AM-3867, in a culture medium and isolating the compound formed and accumulated in the medium from the cultured product. Said frenolicin B is useful as an antibiotic.

1 Claim, 2 Drawing Figures

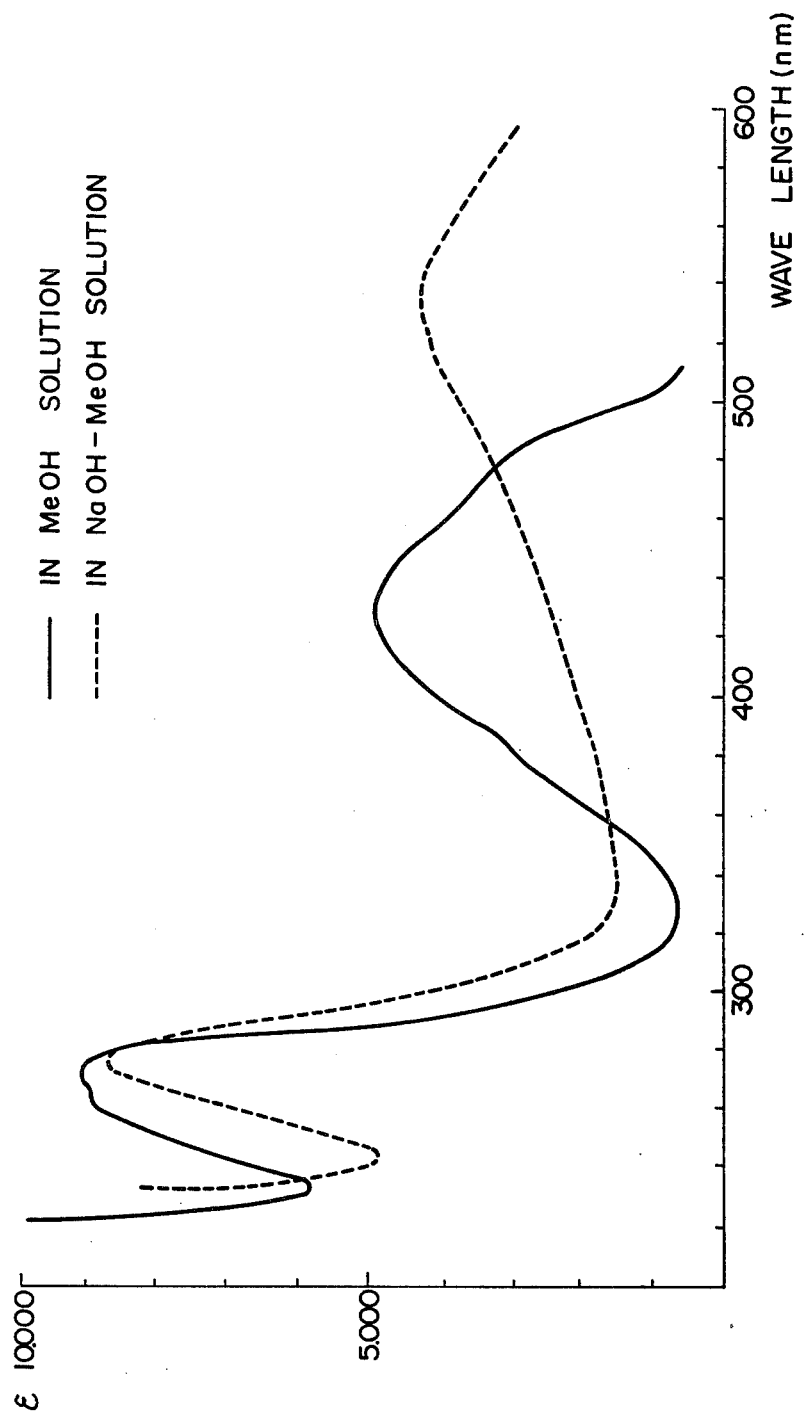

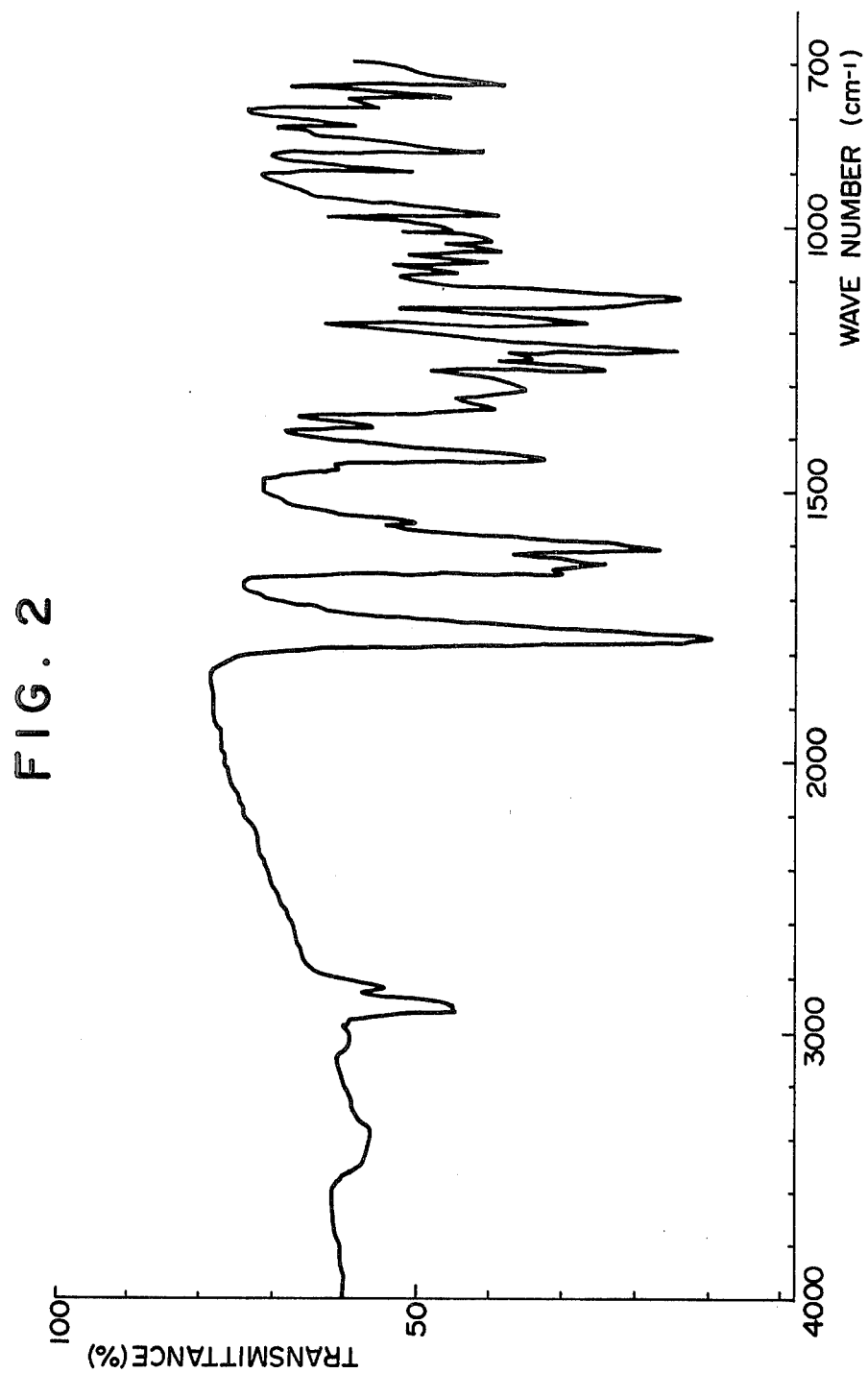

COMPOUND, FRENOLICIN B WHICH IS USEFUL AS AN ANTIBIOTIC

This invention relates to a novel compound particularly useful as antibiotic substance and preparation thereof.

The frenolicin B of the present invention represented by the formula:

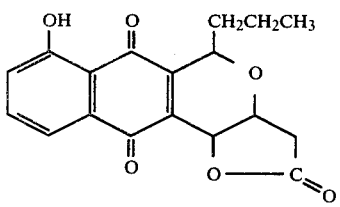

is a novel compound having the following physical and chemical properties.

In the accompanying drawings,

FIG. 1 shows ultraviolet absorption spectrum of the compound frenolicin B; and

FIG. 2 infrared absorption spectrum of said compound.

(1) Elemental analysis

The compound consists of carbon, hydrogen and oxygen, containing no nitrogen, sulfur and halogen. The elemental analysis values found for this compound are as follows: C: 65.96%, H: 4.87%, O: 29.17%.

(2) Molecular weight

The molecular weight (M+, m/e) as determined from mass analysis of this compound is 328.094.

(3) Molecular formula

From the elemental analysis values and the mass analysis value, the molecular formula $C_{18}H_{16}O_6$ is given for the present compound.

(4) Melting point: 157° to 159° C., completely melt at 163° C.

(5) Ultraviolet absorption spectrum

As shown in FIG. 1, in methanol solution, absorption peaks appear at 260 nm ($\epsilon$8954), 270 nm (9020) and 425 nm (4920); while, in alkaline methanol solution, absorption peaks are shifted to 273 nm and 534 nm, and returned to the original values by neutralization of the solution. There is no substantial shift of the absorption in acidic methanol solutions.

(6) Infrared absorption spectrum (KBr method)

As shown in FIG. 2, there is exhibited the presence of absorptions attributable to intramolecular hydrogen bond between hydroxyl groups of polymer (3400 cm$^{-1}$), methyl group and methylene group (2940 cm$^{-1}$), carbonyl group of five-membered lactone ring (1770 cm$^{-1}$), carbonyl group and double bond of 1,4-quinone (1650, 1635 cm$^{-1}$).

(7) Color and crystal form of the substance

Orange colored columnar crystals.

The biological properties of the present compound frenolicin B are set forth below.

(I) Antibacterial property

Table 1 shows anti-mold anti-yeast spectrum (in terms of minimum growth inhibitory concentration) of the present compound according to agar dilution method. Table 2 shows anti-mold anti-yeast spectrum of deoxyfrenolicin. Clearly, the frenolicin B is superior to deoxyfrenolicin. Table 3 also shows the antibacterial spectrum (in terms of minimum inhibitory concentration) against Mycoplasma according to agar dilution method and culture broth dilution method.

Table 1
Anti-mold anti-yeast spectrum of the compound frenolicin B (minimum growth inhibitory concentration: mcg/ml)

| | |
|---|---|
| Candida albicans | 0.78 |
| Saccharomyces cerevisiae | 0.78 |
| Microsporum gypseum | <0.1 |
| Penicillium chrysogenum | 6.25 |
| Trichophyton interdigitale | <0.1 |
| Trichophyton mentagrophytes | 12.5 |
| Piricularia oryzae | <0.1 |
| Aspergillus fumigatus | 6.25 |
| Aspergillus niger | >100 |

Table 2
Anti-mold anti-yeast spectrum of the antibiotic substance deoxyfrenolicin (minimum growth inhibitory concentration, mcg/ml)

| | |
|---|---|
| Candida albicans | 25 |
| Saccharomyces cerevisiae | 25 |
| Microsporum gypseum | 12.5 |
| Penicillium chrysogenum | 50 |
| Trichophyton interdigitale | 12.5 |
| Trichophyton mentagrophytes | 25 |
| Piricularia oryzae | 0.78 |
| Aspergillus fumigatus | 25 |
| Aspergillus niger | >100 |

Table 3
Anti-mycoplasma spectrum of the compound frenolicin B (minimum growth inhibitory concentration, mcg/ml

| | Agar dilution method | Culture broth dilution method |
|---|---|---|
| Mycoplasma gallisepticum Kp-13 | 3.13 | 25 |
| Mycoplasma gallisepticum S-6 | 3.13 | 12.5 |
| Mycoplasma gallisepticum 333P | 3.13 | 12.5 |
| Mycoplasma pneumoniae | 3.13 | 12.5 |
| Acholeplasma laidlawii (A) PG8 | 6.25 | 25 |
| Acholeplasma laidlawii (B) Bm1 | 50 | 100 |

As apparently seen from Table 1 and Table 3, the present compound is considered to be effective for prevention and therapy of infectious diseases caused by eumycetes and mycoplasmas.

The above compound frenolicin B has strong absorption attributable to carbonyl group of five-membered lactone ring at around 1770 cm$^{-1}$ in infra-red absorption spectrum, similarly as Kalafungin (J.A. 21,454, 1968). Its chart is similar to that of deoxyfrenolicin (U.S. Pat. No. 3,452,051, 1969) having no corresponding absorption at 1770 cm$^{-1}$ but having in place thereof strong absorption due to carboxylic acid at 1715 cm$^{-1}$. Its molecular formula is fewer in number of hydrogen atoms by two than that of deoxyfrenolicin.

From the description as set forth above, the present compound frenolicin B is judged to be a novel compound in which lactone ring is formed on deoxyfrenolicin.

As the microorganism strain to be used for producing the compound frenolicin B according to the present invention, there may be mentioned as one example Streptomyces roseofulvus AM-3867.

The microbiological characteristics of this strain are as follows:

(I) Morphological characteristics

Nutrient mycelium is well developped in both synthetic medium and natural agar medium, being irregularly branched but having generally no septum. Aerial mycelium is grown abundantly on glucose-asparagine agar medium, starch-inorganic salt agar medium, oatmeal agar medium, etc.; moderately on nutrient agar medium, glucose-peptone agar medium, glycerol-calcium malate, etc., exhibiting mostly velvety appearance; but only sparingly on glucose-nitrate agar medium, yeast extract-malt extract agar medium, etc. It exhibits a color of brownish white to light orange.

According to microscopic observation, main axis of aerial mycelium is found to be irregularly branched. Its sporangiophore exhibits linear shape, and linkage of 10 or more spores recognized. The size of spores is 0.5 to $0.6\mu \times 0.7$ to $1.0\mu$, being substantially ellipsoidal. The spores have smooth surfaces. None of sclerotium, sporangium and flagella are observed.

(II) Cultural characteristics in various media (Table 4)

The tests are conducted according to the method of E. B. Scharling et al (Int. J. Syst. Bacteriol. vol. 16, p. 313, 1966), and also well-known media and test methods are used in combination. The color tone is determined with reference to standard color diagram of Color Harmony Manual, fourth edition (Container Corporation of America, Chicago, 1958), and color label is indicated together with its code in the bracket. In the following, unless otherwise indicated, there are given the results of observation of culture in respective media after two weeks of cultivation at 27° C.

Table 4

Cultural characteristics of *Streptomyces* sp. AM-3867

| | |
|---|---|
| Sucrose-nitrate agar | G: thin, colorless |
| | R: pearl pink (3ca) |
| | AM: moderate, velvety, pearl pink (3ca) |
| | SP: — |
| Glucose-nitrate agar | G: moderate, colorless |
| | R: pearl pink (3ca) |
| | AM: poor, velvety, pearl pink (3ca) |
| | SP: — |
| Glycerol-calcium malate agar | G: moderate, pearl pink (3ca) |
| | R: pearl pink (3ca) |
| | AM: moderate, velvety, flesh pink (4ca) |
| | SP: flesh pink (5ca) |
| Glucose-asparagine agar (ISP) | G: thin, maple sugar (3ie) |
| | R: yellow maple (3ng) |
| | AM: moderate, velvety, flesh pink (4ca) |
| | SP: — |
| Glycerol-asparagine agar (ISP) | G: moderate, colorless |
| | R: pearl pink (3ca) |
| | AM: moderate, velvety, pearl pink (3ca) |
| | SP: flesh pink (4ca) |
| Inorganic salts-starch agar (ISP) | G: moderate, light tan (3gc) |
| | R: pearl pink (3ca) |
| | AM: abundant, velvety, flesh pink (4ca) |
| | SP: flesh pink (4ca) |
| Tyrosine agar (ISP) | G: thin, colorless |
| | R: pearl pink (3ca) |
| | AM: poor, velvety, pearl pink (3ca) |
| | SP: ± |
| Nutrient agar | G: moderate, light maize (2ea) |
| | R: light maize (2ea) |
| | AM: moderate, velvety, white (a) |
| | SP: light maize (2ea) |
| Glucose-peptone agar | G: moderate, wrinkled, light rose beige (4ec) |
| | R: rose beige (4gc) |
| | AM: moderate, velvety, light ivory (2ca) |
| | SP: light amber (3ic) |
| Yeast extract-malt extract agar (ISP) | G: moderate, maple sugar (3ie) |

Table 4-continued

Cultural characteristics of *Streptomyces* sp. AM-3867

| | |
|---|---|
| | R: topaz (3ne) |
| | AM: poor, velvety, pearl pink (3ca) |
| | SP: topaz (3pe) |
| Oatmeal agar (ISP) | G: thin, light tan (3gc) |
| | R: pearl pink (3ca) |
| | AM: abundant, velvety, flesh pink (4ca) |
| | SP: — |
| Peptone-yeast extract iron agar (ISP) | G: moderate, bamboo (2gc) |
| | R: bamboo (2gc) |
| | AM: very poor |
| | SP: — |

Abbreviations:
G (Growth),
R (Reverse),
AM (Aerial mycelium), and
SP (Soluble pigment)

(III) Physiological characteristics (1) Formation of melanoid pigment: negative (tyrosine agar, peptone-yeast extract iron agar, glucose-peptone-gelatin stab (21°–23° C.), trypton-yeast extract).

(2) Tyrosinaze reaction: negative.

(3) Reduction of nitrates: negative.

(4) Liquefaction of gelatin (in glucose-peptone-gelatin medium): suspected positive.

(5) Hydrolysis of starch: positive.

(6) Coagulation of skim milk (37° C.): negative.

(7) Peptonization of skim milk (37° C.): positive.

(8) Hydrolyzation of cellulose: negative.

(9) Growth temperature range: 20° to 35° C.

(10) Assimilability of carbon sources (in Pridham-Gottlief medium):

Assimilable: D-glucose, D-fructose, D-xylose, L-rhamnose.

More or less assimilable: L-arabinose, sucrose, raffinose.

Not assimilable: L-inositol, D-mannitol.

(IV) Cell wall composition

The diaminopimelic acid occurs as LL-isomer and has glycine, but none of arabinose and galactose are observed.

The microbiological characteristics of the present microorganism as described above can be summarized as follows.

The cell wall composition contains LL-diaminopimelic acid glycine. Morphologically, the present strain forms linear sporangiophore and has smooth spore surfaces. As the various cultural characteristics, the nutrient mycelium is colorless to yellowish brown, which is not changed as the change in pH, and the color tone of aerial mycelium is brownish white to light orange. As soluble pigments, pigments of light orange to yellowish brown are produced in some of media, while no melanoid pigment is formed.

From these results, the present microorganism strain is believed to belong to genus Streptomyces and moreover to the Red Series according to classification by Pridham and Tresner (Bergey's Manual of Determinative Bacteriology, eighth edition, 1974, page 748 to 829).

The present strain is deposited as *Streptomyces roseofulvus* AM-3867 with the Fermentation Research Institute, Agency of Industrial Science and Technology, Chiba-ken, Japan (FERM-P No. 4359) and with The American Type Culture Collection, Maryland, U.S.A.

(ATCC No. 31476) on Jan. 13th, 1978, and on December 26th, 1978, respectively.

As the microorganism to be used in the present invention, there may be used any microorganism capable of producing the compound frenolicin B belonging to genus Streptomyces, including the aforesaid *Streptomyces roseofulvus* AM-3867 and mutant strains thereof obtained by subjecting said strain to mutation treatment.

There may also be employed any kind of carbon source and nitrogen source, which is assimilable by the microorganism strain to be used, in the medium for the present invention. As carbon sources, there may be used glucose, maltose, galactose, starch, dextrin, glycerine, cod liver oil, etc. As nitrogen source, there may be used soybean powders, peptone, yeast extract, yeast, etc. If desired, phosphoric acid salts, salts of magnesium, potassium, calcium, sodium, iron, manganese or others may also be used.

Fermentation is carried out by shaking cultivation or stirring depth cultivation under aeration under aerobic conditions. The cultivation temperature is generally 20° to 35° C. The cultivation is conducted usually for about 100 to 150 hours, and completed at suitable time when the factor of frenolicin B is judged to reach its maximum.

In the culture broth, there are formed and accumulated frenolicin B and a small quantity of deoxyfrenolicin. Both of these compounds can easily be separated from each other by chromatography on silica gel using benzene as eluant.

After completion of the cultivation, frenolicin B is collected from the culture broth. For example, the culture broth is separated into the microorganism cells and the filtrate. The filtrate is subjected to extraction with an organic solvent, which is separable from water and can dissolve frenolicin B, such as ethyl acetate, butyl acetate, benzene, etc. and then the frenolicin B is recovered according to the conventional method generally used in purification of oil-soluble substances. For example, after concentration of the extract, the frenolicin B is isolated therefrom by silica gel column chromatography.

The present invention is further explained with reference to the following Example, which is set forth only for illustrative purpose and should not be construed as limitative of the invention.

EXAMPLE

One hundred ml of a culture medium (pH 7.0) containing 1% glucose, 2% starch, 0.5% yeast extract, 0.5% peptone and 0.4% calcium carbonate is apportioned in a Sakaguchi's flask of 500 ml capacity and sterilized at 120° C. for 15 minutes. To this medium is inoculated *Streptomyces roseofulvus* AM-3867 strain (NRRL No. 11357, FERM-P 4359, ATCC No. 31476), and reciprocal shaking cultivation is carried out at 110 strokes per minute, at 27° C. for 48 hours. This seed-culture (200 ml) is inoculated to 20 liter of a medium (pH 7.0) containing 3% cod liver oil (Ritac R-10, produced by Riken Vitamin Co., Ltd.), 0.5% peptone, 0.3% yeast extract, 0.1% potassium primary phosphate, 0.1% potassium secondary phosphate and 0.1% magnesium sulfate 7-hydrate put in a 30-liter jar fermenter. The aerating cultivation is carried out with agitation at 250 r.p.m. and aeration of 8 liter/hour at 27° C. for 68 hours. The resultant culture broth is subjected to centrifuge to give 17 liter of the culture broth filtrate containing frenolicin B.

The culture broth filtrate is adjusted to pH 2 with 3 N hydrochloric acid, extracted with 5 liter of butyl acetate and then to the butyl acetate is added 2 liter of 1% aqueous sodium hydrogen carbonate solution to effect phase transfer. Further, 3 N hydrochloric acid is added to this 1% aqueous sodium hydrogen carbonate to adjust the solution to pH 2 and then extraction is conducted with 3 liter of ethyl acetate. After the ethyl acetate layer is dehydrated with anhydrous sodium sulfate, the ethyl acetate layer is concentrated under reduced pressure to give 13 g of reddish brown oily product. This product is dissolved in 100 ml of chloroform and the resultant solution is adsorbed on silica gel (Merck Co., Kieselgel 60, 400 g), previously suspended in chloroform and packed in a column and developed using 2.5 liter of chloroform-ethyl acetate (50:1). The eluted solutions are fractionated by fraction collector into fractions of each 15 ml. A part of the eluted solution colored in yellow is subjected to silica gel thin layer chromatography (Merck Co., Kieselgel $GF_{254}$, 0.3 mm; Eluant:benzene:acetone=10:1), and the active fractions No. 53–92 of yellow color, indicating Rf value of 0.55 are collected, concentrated to dryness under reduced pressure, whereby reddish brown powders (1.2 g) are obtained. These powders are dissolved in 15 ml of benzene, adsorbed on silica gel (Merck Co., Kieselgel 60, 50 g), previously suspended in benzene and packed in a column, and then developed with 300 ml of benzene. The eluate is fractionated by fraction collector into fractions of each 10 ml. A part of the yellow colored eluate is subjected to silica gel thin layer chromatography (Merck Co., Kieselgel $GF_{254}$, 0.3 mm, eluant:benzene:acetone=10:1), and fractions No. 11 to 20 containing a substance colored in yellow and indicating Rf value of 0.55 are collected, followed by concentration to dryness under reduced pressure, to give 350 mg of yellowish brown powders. By recrystallization of these powders from a mixed solution of cyclohexane and ethyl acetate, there is obtained 200 mg of orange columnar crystals of frenolicin B.

What we claim is:

1. A compound frenolicin B of the formula:

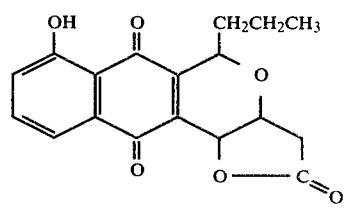

* * * * *